(12) United States Patent
Bouasaysy et al.

(10) Patent No.: US 9,622,896 B2
(45) Date of Patent: Apr. 18, 2017

(54) ENHANCED ASPIRATION PROCESSES AND MECHANISMS FOR INSTRAGASTRIC DEVICES

(75) Inventors: Outhit Bouasaysy, Corona, CA (US); Mark Ashby, Laguna Niguel, CA (US)

(73) Assignee: ReShape Medical, Inc., San Clemente, CA (US)

( * ) Notice: Subject to any disclaimer, the term of this patent is extended or adjusted under 35 U.S.C. 154(b) by 621 days.

(21) Appl. No.: 13/577,612

(22) PCT Filed: Feb. 8, 2011

(86) PCT No.: PCT/US2011/024077
§ 371 (c)(1),
(2), (4) Date: Aug. 28, 2012

(87) PCT Pub. No.: WO2011/097636
PCT Pub. Date: Aug. 11, 2011

(65) Prior Publication Data
US 2013/0035710 A1  Feb. 7, 2013

Related U.S. Application Data

(60) Provisional application No. 61/302,459, filed on Feb. 8, 2010.

(51) Int. Cl.
*A61F 2/00* (2006.01)
*A61F 5/00* (2006.01)
*A61M 25/10* (2013.01)

(52) U.S. Cl.
CPC .......... *A61F 5/0036* (2013.01); *A61F 5/0033* (2013.01); *A61F 5/0043* (2013.01); *A61M 25/1011* (2013.01); *A61M 25/10181* (2013.11); *A61M 25/10185* (2013.11); *A61M 25/1018* (2013.01)

(58) Field of Classification Search
CPC ......... A61M 25/1018; A61B 17/12136; A61B 17/12131; A61F 2/958
USPC .......................................... 606/192
See application file for complete search history.

(56) References Cited

U.S. PATENT DOCUMENTS

| 1,666,690 A | 4/1928 | Drevitson |
| 1,690,995 A | 11/1928 | Pratt |
| 2,493,326 A | 1/1950 | Trinder |
| 2,579,301 A | 12/1951 | Buntin |

(Continued)

FOREIGN PATENT DOCUMENTS

| CA | 2638988 A1 | 5/2007 |
| DE | 8708978 U1 | 11/1987 |

(Continued)

OTHER PUBLICATIONS

Extended European Search Report; Application No. EP11748141.6, Applicant: Reshape Medical, Inc., mailed Feb. 25, 2014, 6 pages.

(Continued)

*Primary Examiner* — Melanie Tyson
*Assistant Examiner* — Rachel S Highland
(74) *Attorney, Agent, or Firm* — Perkins Coie LLP

(57) ABSTRACT

A sealing device attached to an intragastric balloon device having a at least one flexible membrane aligned with and configured to seal an aspiration port of a lumen when the membrane is in a closed state and further configured to provide access to the lumen when the membrane is in a open state.

11 Claims, 13 Drawing Sheets

(56) References Cited

U.S. PATENT DOCUMENTS

| | | |
|---|---|---|
| 3,131,867 A | 5/1964 | Miller et al. |
| 4,133,315 A | 1/1979 | Berman et al. |
| 4,198,983 A | 4/1980 | Becker et al. |
| 4,246,893 A | 1/1981 | Berson |
| 4,356,824 A | 11/1982 | Vazquez |
| 4,368,739 A | 1/1983 | Nelson, Jr. |
| 4,416,267 A | 11/1983 | Garren et al. |
| 4,436,087 A | 3/1984 | Ouchi |
| 4,465,072 A | 8/1984 | Taheri |
| 4,465,818 A | 8/1984 | Shirahata et al. |
| 4,485,805 A | 12/1984 | Foster, Jr. et al. |
| 4,543,089 A | 9/1985 | Moss |
| 4,598,699 A | 7/1986 | Garren et al. |
| 4,694,827 A | 9/1987 | Weiner et al. |
| 4,723,547 A | 2/1988 | Kullas et al. |
| 4,899,747 A | 2/1990 | Garren et al. |
| 4,940,458 A | 7/1990 | Cohn |
| 5,073,347 A | 12/1991 | Garren et al. |
| 5,084,061 A | 1/1992 | Gau et al. |
| 5,123,840 A | 6/1992 | Nates |
| 5,234,454 A | 8/1993 | Bangs |
| 5,259,399 A | 11/1993 | Brown |
| 5,263,934 A | 11/1993 | van den Haak |
| 5,273,536 A | 12/1993 | Savas |
| 5,318,530 A | 6/1994 | Nelson, Jr. |
| 5,334,187 A | 8/1994 | Fischell et al. |
| 5,431,173 A | 7/1995 | Chin et al. |
| 5,496,271 A | 3/1996 | Burton et al. |
| 5,516,812 A | 5/1996 | Chu et al. |
| 5,575,772 A | 11/1996 | Lennox |
| 5,639,810 A | 6/1997 | Smith, III et al. |
| 5,643,209 A | 7/1997 | Fugoso et al. |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,904,701 A | 5/1999 | Daneshvar |
| 5,938,669 A | 8/1999 | Klaiber et al. |
| 5,976,073 A | 11/1999 | Ouchi |
| 5,993,473 A | 11/1999 | Chan |
| 5,997,503 A | 12/1999 | Willis et al. |
| 6,050,274 A | 4/2000 | Gelardi et al. |
| 6,149,621 A | 11/2000 | Makihara |
| 6,179,878 B1 | 1/2001 | Duerig et al. |
| 6,254,355 B1 | 7/2001 | Gharib |
| 6,276,567 B1 | 8/2001 | Diaz et al. |
| 6,280,411 B1 | 8/2001 | Lennox |
| 6,283,951 B1 | 9/2001 | Flaherty et al. |
| 6,423,058 B1 | 7/2002 | Edwards et al. |
| 6,427,089 B1 | 7/2002 | Knowlton |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Stein et al. |
| 6,547,788 B1 | 4/2003 | Maguire et al. |
| 6,579,301 B1 | 6/2003 | Bales et al. |
| 6,592,552 B1 | 7/2003 | Schmidt |
| 6,613,018 B2 | 9/2003 | Bagga et al. |
| 6,613,037 B2 | 9/2003 | Khosravi et al. |
| 6,689,051 B2 | 2/2004 | Nakada |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,627 B2 | 3/2005 | Nozue et al. |
| 6,866,657 B2 | 3/2005 | Shchervinsky et al. |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,939,299 B1 | 9/2005 | Petersen et al. |
| 6,942,680 B2 | 9/2005 | Grayzel et al. |
| 6,958,052 B1 | 10/2005 | Charlton |
| 7,001,419 B2 | 2/2006 | DiCapino et al. |
| 7,016,735 B2 | 3/2006 | Imran et al. |
| 7,020,531 B1 | 3/2006 | Colliou et al. |
| 7,033,373 B2 | 4/2006 | De la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu |
| 7,749,254 B2 | 7/2010 | Sobelman et al. |
| 7,828,749 B2 | 11/2010 | Douglas et al. |
| 7,931,693 B2 | 4/2011 | Binmoeller et al. |
| 8,083,757 B2 | 12/2011 | Gannoe et al. |
| 8,556,925 B2 | 10/2013 | Makower et al. |
| 8,840,952 B2 | 9/2014 | Ashby et al. |
| 8,894,568 B2 | 11/2014 | Pecor et al. |
| 9,050,174 B2 | 6/2015 | Pecor et al. |
| 9,149,611 B2 | 10/2015 | Bouasaysy et al. |
| 2001/0022988 A1 | 9/2001 | Schwartz et al. |
| 2001/0037127 A1 | 11/2001 | De Hoyos Garza |
| 2002/0055757 A1 | 5/2002 | Torre |
| 2002/0107515 A1 | 8/2002 | Edwards et al. |
| 2002/0161388 A1 | 10/2002 | Samuels et al. |
| 2002/0173804 A1 | 11/2002 | Rousseau |
| 2003/0105800 A1 | 6/2003 | Cullen |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garva Alvarez |
| 2004/0059290 A1 | 3/2004 | Palasis |
| 2004/0073162 A1 | 4/2004 | Bleam et al. |
| 2004/0087902 A1 | 5/2004 | Richter |
| 2004/0093058 A1 | 5/2004 | Cottone et al. |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson et al. |
| 2004/0186503 A1 | 9/2004 | DeLegge |
| 2004/0220665 A1 | 11/2004 | Hossainy |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 | 2/2005 | Richard et al. |
| 2005/0027313 A1 | 2/2005 | Shaker |
| 2005/0038415 A1 | 2/2005 | Rohr et al. |
| 2005/0055039 A1 | 3/2005 | Burnett et al. |
| 2005/0059990 A1 | 3/2005 | Ayala |
| 2005/0075624 A1 | 4/2005 | Miesel |
| 2005/0085792 A1 | 4/2005 | Gershowitz |
| 2005/0119674 A1 | 6/2005 | Gingras et al. |
| 2005/0131442 A1 | 6/2005 | Yachia et al. |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192614 A1 | 9/2005 | Binmoeller |
| 2005/0192615 A1 | 9/2005 | Torre et al. |
| 2005/0228504 A1 | 10/2005 | Demarais et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0058829 A1 | 3/2006 | Sampson et al. |
| 2006/0142700 A1 | 6/2006 | Sobelman et al. |
| 2006/0178691 A1 | 8/2006 | Binmoeller |
| 2006/0184112 A1 | 8/2006 | Horn et al. |
| 2006/0259020 A1 | 11/2006 | Sharratt |
| 2006/0270906 A1 | 11/2006 | Matsuno et al. |
| 2007/0016262 A1 | 1/2007 | Gross et al. |
| 2007/0078476 A1 | 4/2007 | Hull et al. |
| 2007/0083224 A1 | 4/2007 | Hively |
| 2007/0093728 A1 | 4/2007 | Douglas et al. |
| 2007/0100367 A1 | 5/2007 | Quijano |
| 2007/0100368 A1 | 5/2007 | Quijano |
| 2007/0100369 A1 | 5/2007 | Cragg |
| 2007/0118168 A1 | 5/2007 | Lointier et al. |
| 2007/0135829 A1 | 6/2007 | Paganon et al. |
| 2007/0142770 A1 | 6/2007 | Rioux et al. |
| 2007/0149994 A1 | 6/2007 | Sosnowski |

(56) References Cited

U.S. PATENT DOCUMENTS

| | | |
|---|---|---|
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0085887 A1 | 4/2008 | Didiuk et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0190363 A1 | 8/2008 | Chen et al. |
| 2008/0208135 A1 | 8/2008 | Annunziata et al. |
| 2008/0208241 A1 | 8/2008 | Weiner et al. |
| 2008/0233167 A1 | 9/2008 | Li et al. |
| 2008/0243071 A1 | 10/2008 | Quijano |
| 2008/0243166 A1* | 10/2008 | Paganon et al. ............ 606/192 |
| 2008/0255601 A1 | 10/2008 | Birk |
| 2008/0312679 A1 | 12/2008 | Hardert et al. |
| 2008/0319471 A1 | 12/2008 | Sosnowski et al. |
| 2009/0048624 A1 | 2/2009 | Alverdy |
| 2009/0259236 A2 | 10/2009 | Burnett et al. |
| 2009/0275973 A1 | 11/2009 | Chen et al. |
| 2009/0287231 A1 | 11/2009 | Brooks et al. |
| 2010/0023047 A1 | 1/2010 | Simpson |
| 2010/0049224 A1 | 2/2010 | Vargas |
| 2010/0063530 A1 | 3/2010 | Valencon et al. |
| 2010/0130998 A1 | 5/2010 | Alverdy |
| 2010/0174307 A1 | 7/2010 | Birk et al. |
| 2010/0191270 A1 | 7/2010 | Garza et al. |
| 2010/0234853 A1 | 9/2010 | Pecor et al. |
| 2010/0243135 A1 | 9/2010 | Pepper et al. |
| 2010/0251837 A1 | 10/2010 | Bouasaysy et al. |
| 2011/0172767 A1 | 7/2011 | Rathi et al. |
| 2011/0178544 A1 | 7/2011 | Sosnowski et al. |
| 2011/0276076 A1 | 11/2011 | Paganon |
| 2011/0295300 A1 | 12/2011 | Verd et al. |
| 2012/0191126 A1 | 7/2012 | Pecor et al. |
| 2012/0271336 A1 | 10/2012 | Hamman et al. |
| 2012/0271338 A1 | 10/2012 | Bouasaysy et al. |
| 2012/0289992 A1 | 11/2012 | Quijano et al. |
| 2013/0053880 A1 | 2/2013 | Bouasaysy et al. |
| 2013/0102876 A1 | 4/2013 | Limon et al. |
| 2013/0261654 A1 | 10/2013 | Bouasaysy et al. |
| 2013/0296914 A1 | 11/2013 | Quijano et al. |
| 2014/0031850 A1 | 1/2014 | Bouasaysy et al. |
| 2014/0257358 A1 | 9/2014 | Alverdy et al. |
| 2014/0371775 A1 | 12/2014 | Ashby et al. |
| 2015/0216529 A1 | 8/2015 | Kwok et al. |
| 2015/0238342 A1 | 8/2015 | Sosnowski et al. |
| 2015/0265811 A1 | 9/2015 | Pecor |
| 2015/0366691 A1 | 12/2015 | Bouasaysy |
| 2016/0008156 A1 | 1/2016 | Pecor et al. |

FOREIGN PATENT DOCUMENTS

| | | |
|---|---|---|
| EP | 0103481 | 3/1984 |
| EP | 0457456 | 5/1990 |
| EP | 0485903 | 8/1991 |
| EP | 1781183 | 5/2007 |
| FR | 2862525 | 5/2005 |
| FR | 2892297 | 4/2007 |
| GB | 2090747 A | 7/1982 |
| GB | 2139902 | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| JP | 2009285135 A | 12/2009 |
| JP | 2015154964 A | 8/2015 |
| JP | 2016127954 | 7/2016 |
| WO | 8805671 A1 | 8/1988 |
| WO | 9000369 A1 | 1/1990 |
| WO | 9925418 A1 | 5/1999 |
| WO | WO-0141700 | 6/2001 |
| WO | WO-0166166 A2 | 9/2001 |
| WO | WO-0240081 | 5/2002 |
| WO | 2005082296 A1 | 9/2005 |
| WO | 2005107641 A2 | 11/2005 |
| WO | 2005120363 A1 | 12/2005 |
| WO | WO2006035446 | 4/2006 |
| WO | WO2006056944 | 6/2006 |
| WO | WO2006/128978 | 12/2006 |
| WO | WO-2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO2008121831 | 10/2008 |
| WO | WO-2009055386 A2 | 4/2009 |
| WO | WO2009112786 | 9/2009 |
| WO | WO-2010048021 | 4/2010 |
| WO | WO2010115161 | 10/2010 |
| WO | WO2011011629 | 1/2011 |
| WO | WO2011011741 | 1/2011 |
| WO | WO2011011743 | 1/2011 |
| WO | WO2011038270 | 3/2011 |
| WO | WO2011024077 | 8/2011 |
| WO | WO2011097637 | 8/2011 |
| WO | WO2011127205 | 10/2011 |
| WO | WO2012048226 | 4/2012 |

OTHER PUBLICATIONS

Final Office Action; U.S. Appl. No. 13/858,767, Mailing Date May 22, 2103, 12 pages.

Extended European Search Report; Application EP11740536.5, Applicant: ReShape Medical, Inc., mailed Jul. 3, 2014, 8 pages.

Extended European Search Report; Application EP11831683.5, Applicant: Reshape Medical, Inc., mailed Jul. 3, 2014, 8 pages.

Final Office Action; U.S. Appl. No. 13/556,032, mailed on Jan. 28, 2014, 8 pages.

Non-Final Office Action; U.S. Appl. No. 13/386,650 mailed on Jun. 3, 2014, 15 pages.

Notice of Allowance; U.S. Appl. No. 12/753,803, dated May 13, 2014, 18 pages.

Ostrovsky, ReShape Inflatable Gastric Balloon going on Trial as Weight Loss Option; http://www.medgadget.com/2010/02/re-shape_inflatable_gastric_balloon_system_going_on_trial_as_weight_loss_option.html Feb. 4, 2010. retrieved on Feb. 10-Feb. 13.

European Supplementary Search Report; EP Application No. 10802994.3, Applicant: ReShape Medical, Inc., mailed Jun. 28, 2013, 8 pgs.

European Supplementary Search Report; EP Application No. 10802918.2, Applicant: ReShape Medical, Inc., mailed Jun. 5, 2013, 6 pgs.

Extended European Search Report; Application No. EP11766679.2; Applicant: Reshape Medical, Inc., mailed Dec. 12, 2013, 6 pages.

European Search Report-Supplementary; EP 03726447.0, Applicant: Applied Medical Resources Corporation: Mar. 1, 2006, 3 pgs.

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043134; Applicant: ReShape Medical, Inc., Mailing Date Apr. 27, 2011, 12 pages.

International Search Report; International Application No. PCT/US2010/043136; Applicant: ReShape Medical, Inc., Mailing Date Apr. 12, 2011, 9 pages.

(56) References Cited

OTHER PUBLICATIONS

International Search Report; International Application No. PCT/US2010/050260; Applicant: ReShape Medical, Inc., Mailing Date: Jun. 17, 2011, 9 pages.
International Search Report; International Application No. PCT/US2011/026233; Applicant: ReShape Medical, Inc., Mailing Date Apr. 26, 2011, 9 pages.
International Search Report; International Application No. PCT/US2011/031463; Applicant: ReShape Medical, Inc., Mailing Date: Jun. 27, 2011, 10 pages.
International Search Report; International Application No. PCT/US2003/012782, Applicant: Applied Medical Resources Corporation, dated: Oct. 28, 2003, 7 pages.
International Search Report; International Application No. PCT/US2006/042336, Applicant: Abdominus, Inc., dated: Mar. 14, 2007, 9 pages.
International Search Report; International Application No. PCT/US2006/042710, Applicant: Abdominus, Inc. et al., dated: Mar. 15, 2007, 9 pages.
International Search Report; International Application No. PCT/US2006/042711, Applicant: Abdominus, Inc. et al, dated: Mar. 16, 2007, 9 pages.
International Search Report; International Application No. PCT/US2006/048647, Applicant: Abdominus, Inc. et al., dated: May 22, 2007, 12 pages.
International Search Report; International Application No. PCT/US2008/058677, Applicant: ReShape Medical et al., dated: Aug. 21, 2008, 12 pages.
International Search Report; International Application No. PCT/US2008/068058, Applicant: ReShape Medical, Inc. et al, dated: Nov. 19, 2008, 11 pages.
International Search Report; International Application No. PCT/US2010/029865, Applicant: ReShape Medical, Inc., dated: Jan. 5, 2011, 9 pages.
International Search Report; International Application No. PCT/US2011/024077; Applicant: ReShape Medical, Inc., dated: Apr. 6, 2011, 12 pages.
International Search Report; International Application No. PCT/US2011/024082, Applicant: ReShape Medical, Inc., dated: Apr. 6, 2011, 10 pages.
International Search Report; International Application No. PCT/US1155373, Applicant: Reshape Medical, Inc., dated: Jan. 20, 2012, 7 pages.
"Living with the BIB: BioEnterics Intragastric Balloon Program: Patient Information"; INAMED Health: Bioenteris Corporation, ECO-SBA-10434; dated Apr. 20, 2004 and May 14, 2005, located online at: www.sydneyobesity.com.au/pdf/M946-01.pdf; 10 pages.
Non-Final Office Action; U.S. Appl. No. 11/263,302; dated: Oct. 9, 2012, 6 pages.
Non-Final Office Action; U.S. Appl. No. 11/694,536; dated: Oct. 26, 2011, 13 pages.
Non-Final Office Action; U.S. Appl. No. 12/723,545; dated Feb. 29, 2012, 10 pages.
Non-Final Office Action; U.S. Appl. No. 12/625,473; dated Oct. 24, 2011, 18 pages.
Non-Final Office Action; U.S. Appl. No. 12/625,473; dated Jul. 12, 2012; 10 pages.
Non-Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
"ReShape Inflatable Gastric Balloon Going on Trial as Weight Loss Option," MedGadget: Internet Journal of Emerging Medical Technologies. Feb. 4, 2010, 5 pages.
Wahlen CH et al. "The BioEnterics Intragastric Balloon: How to use it" Obesity Surgery 2001; 11:524-527.
Extended European Search Report; Application No. EP6827098.3, Applicant: Reshape Medical, Corporation, mailed on Aug. 25, 2014, 3 pages.
Extended European Search Report; Application No. EP6827314.3, Applicant: ReShape Medical Corporation, mailed Aug. 1, 2014, 3 pages.
Extended European Search Report; Application No. EP6827313.5, Applicant: ReShape Medical Corporation, mailed Jul. 30, 2014, 5 pages.
Extended European Search Report; Application No. EP6847847.8, Applicant ReShape Medical Corporation, mailed Aug. 14, 2014, 5 pages.
Final Office Action; U.S. Appl. No. 13/858,767, mailed on May 30, 2014, 12 pages.
Non-Final Office Action; U.S. Appl. No. 13/386,638, mailed on Jun. 27, 2014, 12 pages.
Canadian Office Action: Application No. CA 2680124, Applicant: Reshape Medical Corporation, mailed Nov. 4, 2014, 3 pages.
Canadian Office Action; Application No. 2,691,530, mailed Dec. 18, 2014, 4 pages.
Canadian Office Action; Application No. CA 2638163, Applicant: Reshape Medical Corporation, mailed Mar. 10, 2015, 4 pages.
Canadian Office Action; Application No. CA 2638988, Applicant Reshape Medical Corporation, mailed Dec. 22, 2014 3 pages.
Canadian Office Action; Application No. CA 2638988, Applicant Reshape Medical Corporation, mailed Mar. 6, 2014, 4 pages.
Canadian Office Action; Application No. CA 2638989, Applicant: Reshape Medical Corporation, mailed May 22, 2013 3 pages.
Canadian Office Action; Application No. CA 2640554, Applicant: Reshape Medical Corporation, mailed May 27, 2013, 2 pages.
Canadian Office Action; Application No. CA2484838, Applicant: Reshape Medical, Inc., mailed Nov. 13, 2009, 3 pages.
Canadian Office Action; Application No. CA2484838, Applicant: Reshape Medical, Inc., mailed Sep. 24, 2010, 3 pages.
Canadian Office Action; Application No. CA2638163, Applicant: Reshape Medical Corporation, mailed Jul. 17, 2013, 2 pages.
Canadian Office Action; Application No. CA2638988, Applicant: Reshape Medical Corporation, mailed May 28, 2013, 3 pages.
Canadian Office Action; Application No. CA2780085, Applicant: Reshape Medical, Inc., mailed Jul. 23, 2012, 2 pages.
European Examination Report; Application No. 03726447.0, Applicant: Applied Medical Resources Corporation: Oct. 26, 2007, 4 pages.
European Examination Report; Application No. EP108002918.2, Applicant: Reshape Medical Inc., mailed Dec. 17, 2014, 5 pages.
European Examination Report; Application No. EP108029943, Applicant: Reshape Medical Inc., mailed Dec. 18, 2014, 4 pages.
European Examination Reported; Application No. 08771842.5, May 7, 2015, 5 pages.
European Supplementary Search Report; Application No. 08771842.5, Apr. 24, 2015, 3 pages.
Extended European Search Report; Application No. 08732989.2, Applicant: Reshape Medical, Inc., mailed Oct. 16, 2014, 7 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. 2014-52972; mailed Feb. 25, 2015, 7 pages.
Japanese Office Action; Application No. JP2010-501261, mailed Sep. 7, 2012, 10 pages.
Japanese Office Action; Application No. JP2010-515040, mailed Jan. 7, 2013, 18 pages.
Japanese Office Action; Application No. JP2012-503759, mailed Mar. 24, 2014, 5 pages.
Japanese Office Action; Application No. JP2013-43712, mailed Jan. 8, 2015, 8 pages.
Japanese Office Action; Application. No. JP2013-043712, mailed Apr. 22, 2013, 5 pages.
Canadian 2nd Office Action Application No. 2680124, Applicant: ReShape Medical, Inc., mailed Jul. 9, 2015, 3 pages.
European Examination Report; Application No. 06827313.5, Applicant: ReShape Medical Inc., mailed Jul. 13, 2015, 5 pages.
European Examination Report; Application No. 06847847.8, Applicant: ReShape Medical Inc., mailed Jul. 13, 2015, 4 pages.

(56) References Cited

OTHER PUBLICATIONS

Japanese Office Action; Application No. 2013-532976, Applicant: ReShape Medical, Inc., mailed Jun. 26, 2015, 10 pages.
European Search Report for European Application No. 11740535.7, Applicant: ReShape Medical, Inc., mailed Mar. 8, 2016, 14 pages.
Cronin, C. G. et al., "Normal small bowel wall characteristics on MR enterography," European Journal of Radiology 74(2):207-211, Aug. 2010.
European Search Report for Application No. 15198773 dated Jul. 15, 2016, 7 pages.
Gray, H.; "Anatomy of the Human Body;" Philadelphia: Lea & Febiger, 1918; Section XI Splanchnology, 2g; "The Small Intestine;" Bartleby.com, 2000. Web. URL: www.bartleby.com/107/248.html. Accessed: Oct. 26, 2015. 12 pages.
Chou,Chou, C. et al., "Structural Effects on the Thermal Properties of PDPS/PDMS Copolymers," Journal of Thermal Analysis, vol. 40, pp. 657-667, 1993.
European Examination Report; Application No. 11766679.2, Applicant: Reshape Medical Inc., mailed Dec. 1, 2016, 4 pages.
European Examination Report; Application No. 11748141.6, Applicant: Reshape Medical Inc., mailed Dec. 8, 2016, 3 pages.
Extended European Search Report; Application No. 16183882.6, Applicant: Reshape Medical Inc., mailed Feb. 17, 2017, 9 pages.

\* cited by examiner

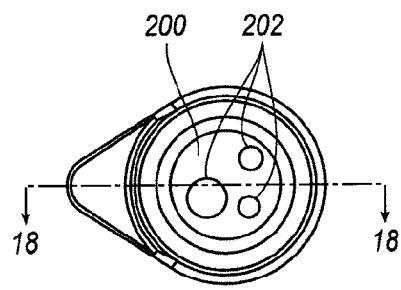
Fig. 17
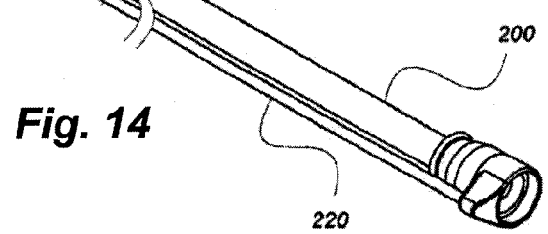
Fig. 14
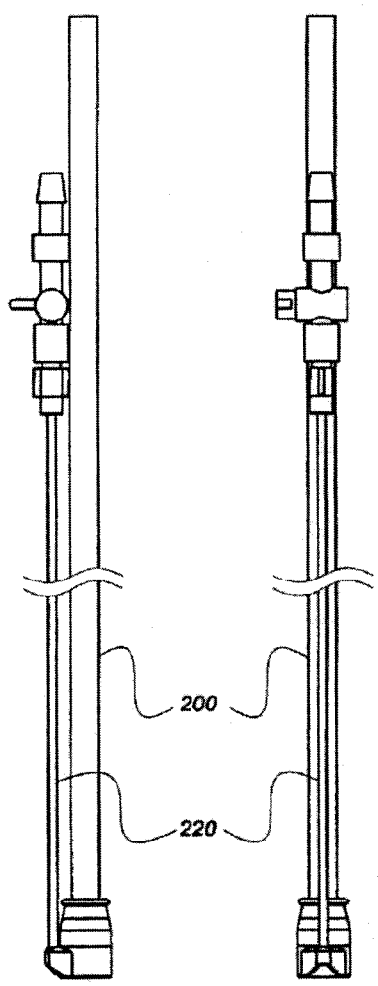
Fig. 15    Fig. 16
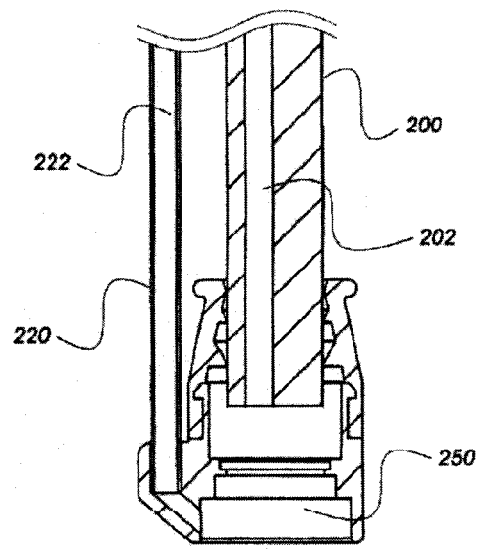
Fig. 18

ENHANCED ASPIRATION PROCESSES AND MECHANISMS FOR INSTRAGASTRIC DEVICES

CROSS-REFERENCE TO RELATED APPLICATION(S)

The present application is a U.S. National Phase application under 35 U.S.C. 371 of International Application Serial No. PCT/US2011/024077, filed Feb. 8, 2011, which claims the benefit of U.S. Provisional Patent Application Ser. No. 61/302,459, filed Feb. 8, 2010, the entire contents of which are incorporated herein by reference in their entireties.

RELATED REFERENCES

This application incorporates by reference: U.S. Pat. Pub. No. 2007/0100367, published May 3, 2007; U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; U.S. Pat. Pub. No. 2008/0243071, published Oct. 2, 2008; U.S. Pat. Pub. No. 2008/0319471, published Dec. 25, 2008; U.S. Pat. Pub. No. 2005/0159769, published Jul. 21, 2005; U.S. Pat. Pub. No. 2009/0048624, published Feb. 19, 2009; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; each as if fully set forth herein in its entirety.

BACKGROUND

This disclosure relates to implantable, expandable gastric devices. In particular, this disclosure relates to mechanisms and procedures for controlled deflation and explant of such devices.

Many conventional implantable gastric devices have a balloon filled with a biocompatible fluid. Such gastric devices are generally inserted into the stomach when the balloon is deflated and then inflated in vivo. The gastric devices are often left in the stomach for an extended period of time to treat severe obesity or other conditions. The gastric devices are eventually removed after completing the treatment or for other reasons by deflating the balloon, grasping the gastric device with an extraction tool, and extracting the gastric device via the esophagus and mouth. Conventional gastric devices are deflated by attempting to puncture the balloon and aspirate the biocompatible fluid through a needle.

One challenge of deflating conventional devices is that the balloon may rupture when it is punctured by the needle. For example, the balloon typically degrades over time because stomach acids, fungi, and bacteria may degrade the integrity of the balloon wall, and the needle puncture may cause a degraded balloon wall to fail. Also, it is difficult to control the angle between the needle and the balloon, and the needle will tend to rip the balloon as opposed to puncturing the balloon at certain angles. When the balloon ruptures, the biocompatible fluid is quickly expelled into the stomach, which complicates the extraction procedure and may be uncomfortable to the patient.

Another challenge of implantable gastric devices is grasping the device for extraction. Several existing devices are grasped by a claw or snare. These procedures can be challenging because projections and/or other features that are easy to grasp may agitate the stomach wall. Thus, there is a need to improve the deflation and extraction of implantable gastric devices.

BRIEF DESCRIPTION OF THE DRAWINGS

Several embodiments of the present technology are described and shown with reference to the following description taken in conjunction with the accompanying drawings wherein like reference numerals denote like elements.

FIG. 14 shows a partial perspective view of an endoscope with suction device.

FIG. 15 shows a partial side view of an endoscope with suction device.

FIG. 16 shows a partial side view of an endoscope with suction device.

FIG. 17 shows an end view of an endoscope with suction device.

FIG. 18 shows a partial sectional view of an endoscope with suction device.

DETAILED DESCRIPTION

Figure 1:
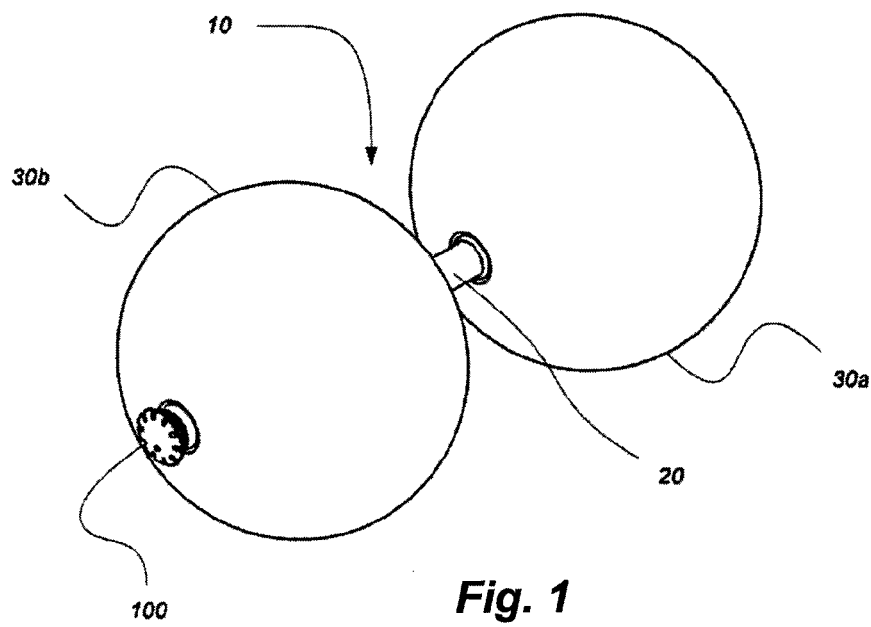
FIG. 1 shows a perspective view of an intragastric device.

Specific details of several embodiments of the present technology are described below with reference to an intragastric device with a sealing device and methods for implanting and explanting such devices. Although many of the embodiments are described below with respect to a dual balloon intragastric device, but other types of devices with only one balloon or more than two balloons may be within the scope of the technology. Moreover, several other embodiments of the technology can have different configurations, components, or procedures than those described in this section. A person of ordinary skill in the art, therefore, will accordingly understand that the technology may have other embodiments with additional elements, or the technology may have other embodiments without several of the features shown and described below with reference to FIGS. 1-19.

Several embodiment of the present technology are directed to a sealing device for use with an intragastric device comprising a body fixedly attached to an intragastric balloon device and a head attached to the body. The sealing device can have at least one flexible membrane aligned with and configured to seal an aspiration port of a lumen when the membrane is in a closed state. The sealing device can be further configured to provide access to the lumen when the membrane is in a open state (e.g., when a needle is passed through the membrane).

Additional embodiments of the technology are directed to an intragastric balloon device comprising a shaft having a plurality of lumens and a plurality of balloons carried by the shaft. Each balloon can be fluidically coupled to a corresponding lumen of the shaft such that an interior portion of each balloon is in fluid communication with its corresponding lumen. The intragastric balloon device can further include a sealing device having a body fixedly attached to the shaft and/or one of the balloon. The sealing device can also have a head attached to the body and at least one flexible membrane configured to seal an aspiration port of one of the lumens when the membrane is in a closed state and to provide fluidic access to the lumen when the membrane is in a open state.

Still additional embodiments of the present technology are directed to a method of aspirating an intragastric balloon device, comprising providing an endoscope device to the intragastric balloon device within a gastric cavity. The intragastric balloon device includes at least one fluid-filled balloon and a sealing device with a body fixedly attached to the intragastric balloon device. The sealing device further includes a head attached to the body and at least one flexible membrane configured to seal an aspiration port of a lumen of the intragastric device when the membrane is in a closed state and to provide fluidic access to the lumen when the membrane is in a open state. The method can further comprise securing the endoscope device to at least a portion of the sealing device, penetrating the membrane of the sealing device with an aspiration device, whereby access to fluid in the corresponding lumen is achieved, and aspirating the fluid from the at least one balloon via the lumen.

In one embodiment, an intragastric device 10 may include at least one collapsible, space-filling component, such as a balloon. As shown in FIG. 1, a plurality of balloons (e.g., first balloon 30*a* and second balloon 30*b*) may be fixed to shaft 20 of intragastric device 10.

Figure 2:
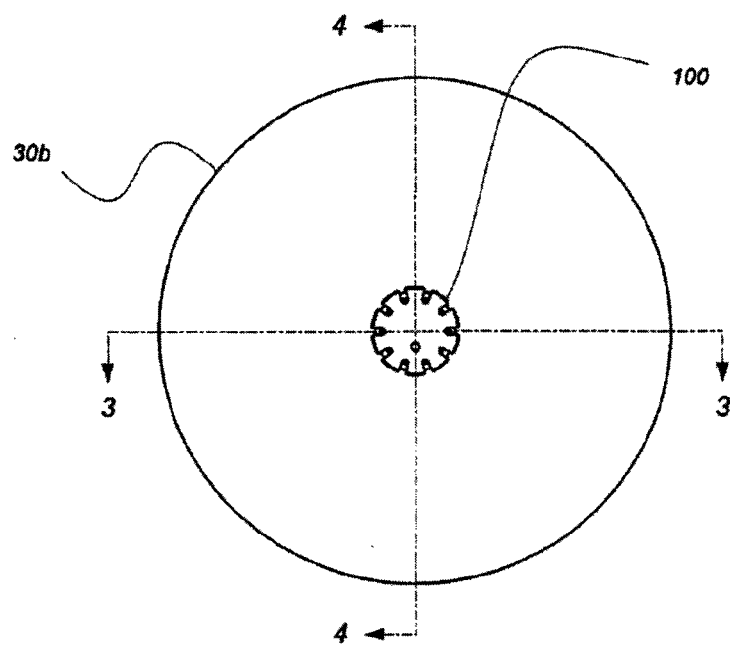
FIG. 2 shows an end view of an intragastric device.
Figure 3:
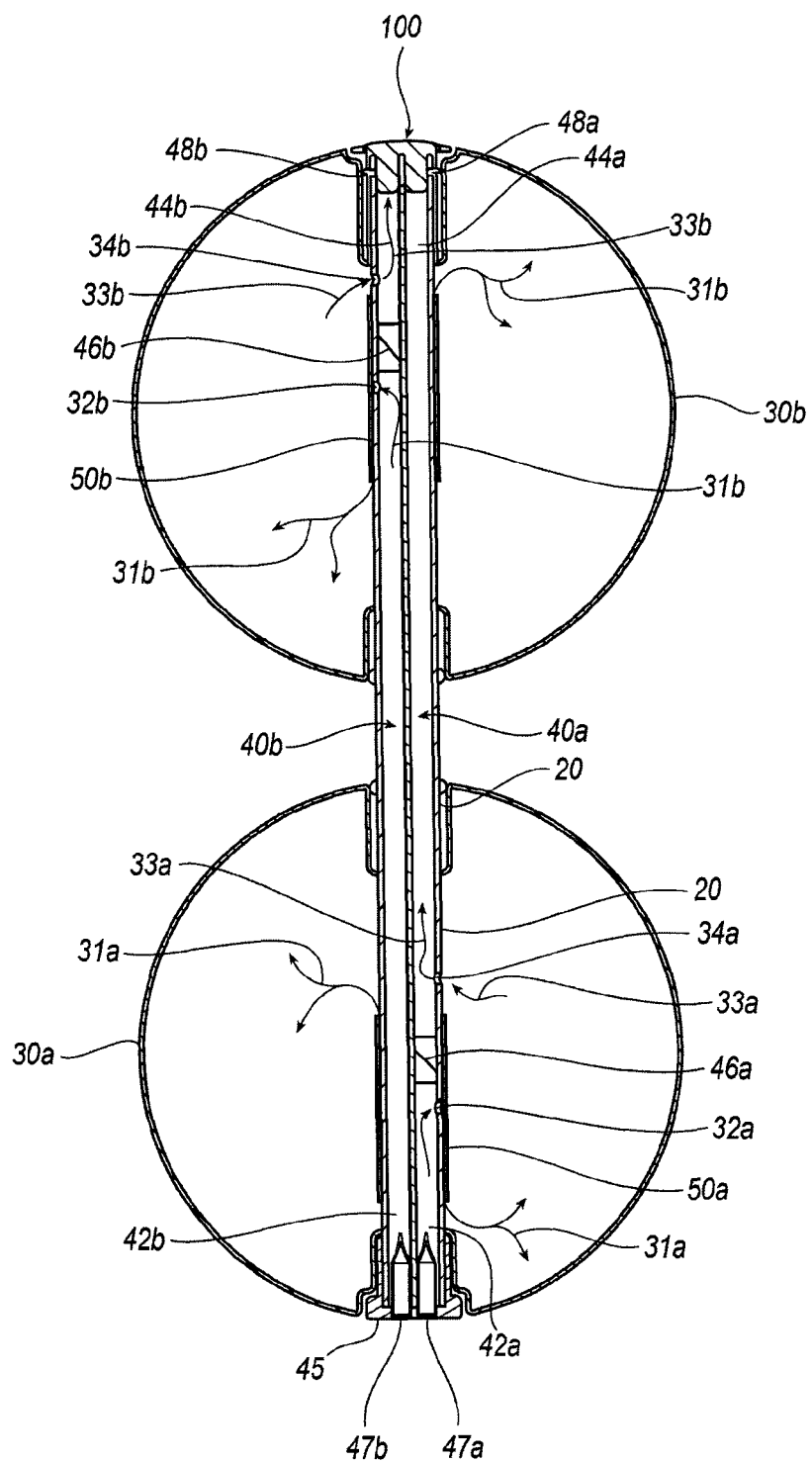
FIG. 3 shows a sectional view of the intragastric device of FIG. 2.

In the particular embodiments of the technology shown in FIGS. 1-3, the intragastric device 10 may include or be configured to interface with sealing device 100 at an end of the intragastric device 10 and a plug 45 at another end of the intragastric device 10. As used herein, the terms "proximal", "distal", "first", and "second" refer to relative locations and orientations of structures, devices, and components. For example, the terms "proximal", "distal", "first", and "second" may be understood to refer to relative identifiers, rather than absolute identifiers except where expressly stated as such. As those having skill in the relevant art will recognize, variation and modification of the disclosure on the same basis is considered within the present disclosure.

Referring to FIG. 3, the shaft 20 of the intragastric device 10 may include a plurality of lumens in which each lumen corresponds to a balloon of intragastric device 10. For example, first lumen 40*a* may provide fluid communication from first inflation port 47*a* to an interior portion of first balloon 30*a* via first inflation opening 32*a*. Likewise, second lumen 40*b* may provide fluid communication from second inflation port 47*b* to an interior portion of second balloon 30*b* via second inflation opening 32*b*.

According to embodiments, and as shown in FIG. 3, each lumen may have a corresponding inflation port at an end of the lumen. Inflation ports may be configured to allow infusion of fluids into corresponding lumens and inhibit or prevent exit of fluids from the same. Inflation ports may include check valves, clack valve, non-return valve, one-way valve, duckbill valves, reed valves, etc. For example, a plug 45 may be positioned at the end of the first balloon 30*a* to dispose the first inflation port 47*a* at an end of first lumen 40*a* and to dispose the second inflation port 47*b* at an end of second lumen 40*b*.

According to embodiments, and as shown in FIG. 3, each lumen of shaft 20 may be divided into inflation and aspiration chambers. For example, first lumen 40*a* may be divided into first inflation chamber 42*a* and first aspiration chamber 44*a* by first barrier 46*a*. Likewise, second lumen 40*b* may be divided into second inflation chamber 42*b* and second aspiration chamber 44*b* by second barrier 46*b*. Such barriers may partition a lumen into at least two separate chambers that may be fluidly connected via the interior portion of a corresponding balloon.

According to embodiments, each balloon may have an opening that fluidly connects the interior portion of the balloon with at least a portion of a corresponding lumen. According to embodiments, and as shown in FIG. 3, each balloon may have a plurality of openings that connect the interior portion of the balloon with disparate chambers of a corresponding lumen. For example, first inflation opening 32*a* may provide a fluid connection between the interior of first balloon 30*a* and first inflation chamber 42*a*, and first aspiration opening 34*a* may provide a fluid connection between the interior of first balloon 30*a* and first aspiration chamber 44*a*.

Figure 3A:
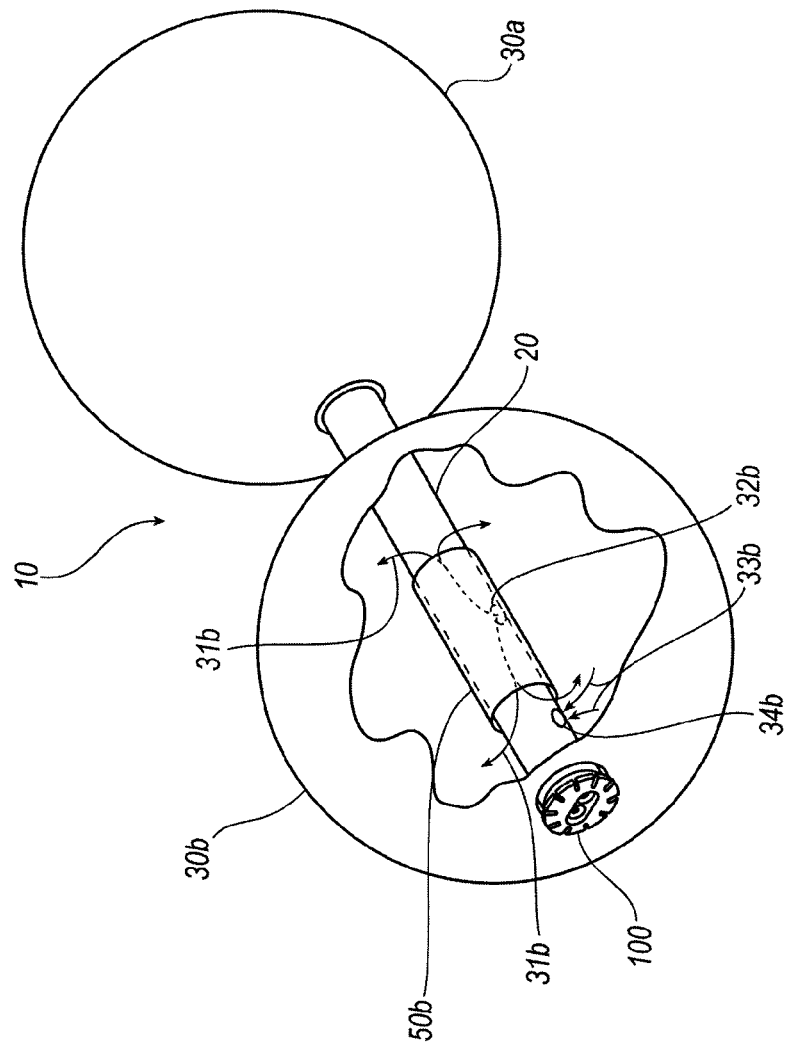
FIG. 3A shows the perspective view of FIG. 1 with a cut-out showing internal features of the intragastric device of FIG. 1.

According to embodiments, and as shown in FIGS. 3 and 3A, sleeves may be provided, each within the interior of a balloon and covering an inflation opening. Such sleeves may provide inflation of the balloon from the corresponding lumen while inhibiting or preventing deflation through the same opening. The sleeves may wrap radially around the portion of shaft 20 near the corresponding opening. For example, first sleeve 50*a* may be provided within the interior portion of first balloon 30*a* and covering at least first inflation opening 32*a*. Likewise, second sleeve 50*b* may be provided within the interior portion of second balloon 30*b* and covering at least second inflation opening 32*a*. Sleeves may inhibit or prevent undesirable fluid pressure on inflation ports and thereby reduce leakage and associated issues. For example, when pressure within the balloon exceeds pressure in the corresponding lumen, a sleeve may be pressed against the corresponding opening to inhibit or prevent leakage into the lumen. When pressure within the lumen exceeds pressure within the corresponding balloon, a sleeve may separate from the corresponding opening and permit infusion into the balloon via a space formed between the sleeve and shaft housing the lumen. Fluid flowing from first inflation chamber 42*a*, through first inflation opening 32*a*, through a space formed between first sleeve 50*a* and the exterior surface of shaft 20, and into the interior of first balloon 30*a* is shown schematically by flow arrows 31*a*. Fluid flowing from the interior of first balloon 30*a*, through first aspiration opening 34*a*, and into first aspiration chamber 44*a* is shown schematically by flow arrows 33*a*. Likewise, second inflation opening 32*b* may provide a fluid connection between the interior of second balloon 30*b* and second inflation chamber 42*b*, and second aspiration opening 34*b* may provide a fluid connection between the interior of second balloon 30*b* and second aspiration chamber 44*b*. Fluid flowing from second inflation chamber 42*b*, through second inflation opening 32*b*, through a space formed between second sleeve 50*b* and the exterior surface of shaft 20, and into the interior of second balloon 30*b* is shown schematically by flow arrows 3 lb. Fluid flowing from the interior of second balloon 30*b*, through second aspiration opening 34*b*, and into second aspiration chamber 44*b* is shown schematically by flow arrows 33*b*.

According to embodiments, and as shown in FIG. 3, each lumen may have a corresponding aspiration port at an end of the lumen. Aspiration ports may be selectively covered by sealing device 100, as further disclosed herein. For example, first aspiration port 48*a* may be provided at an end of first lumen 40*a*. Likewise, second aspiration port 48*b* may be provided at an end of second lumen 40*b*.

Figure 4:
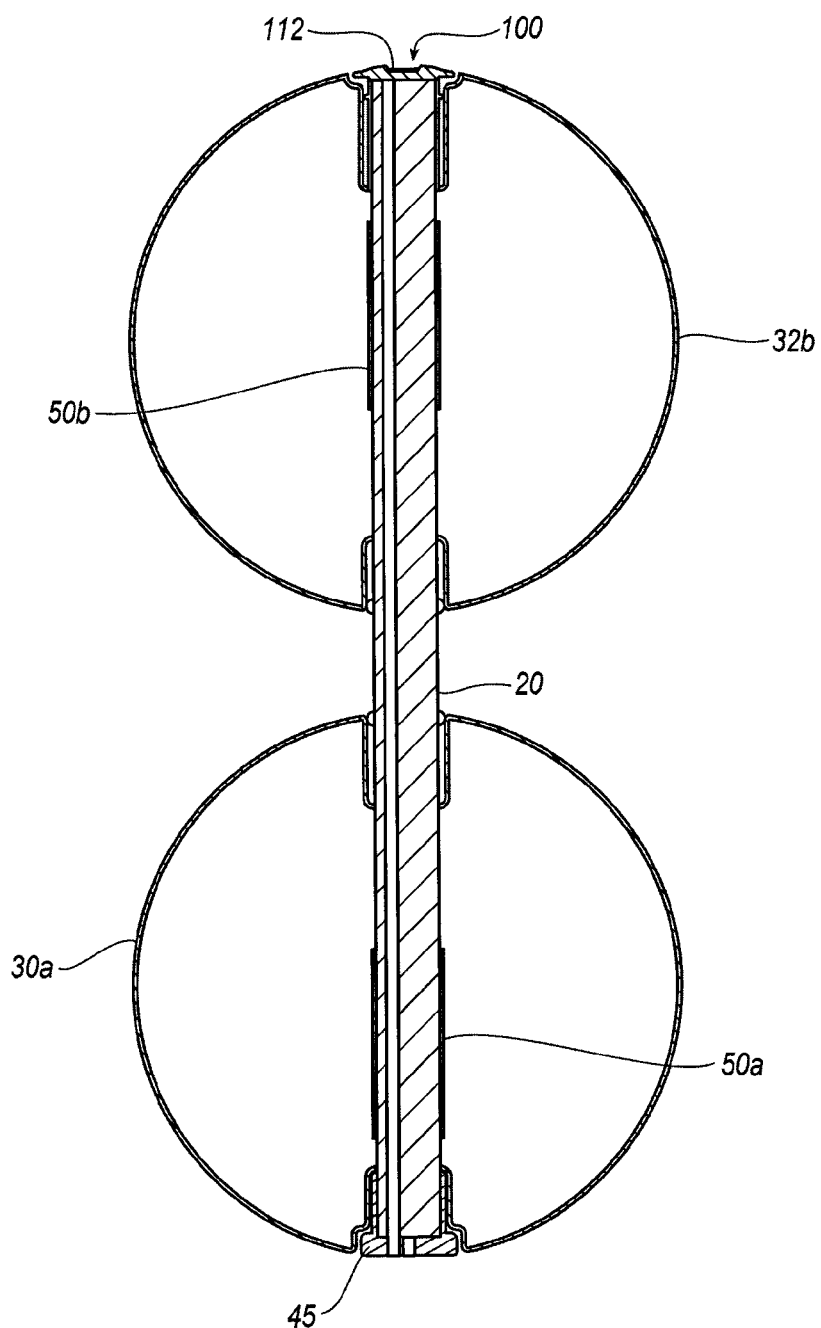
FIG. 4 shows a sectional view of the intragastric device of FIG. 2.
Figure 9:
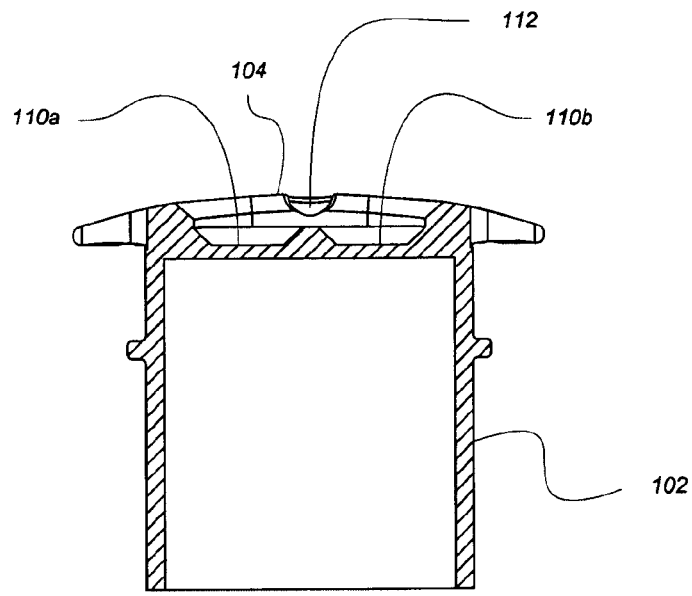
FIG. 9 shows a sectional view of the sealing device of FIG. 7.
Figure 10:
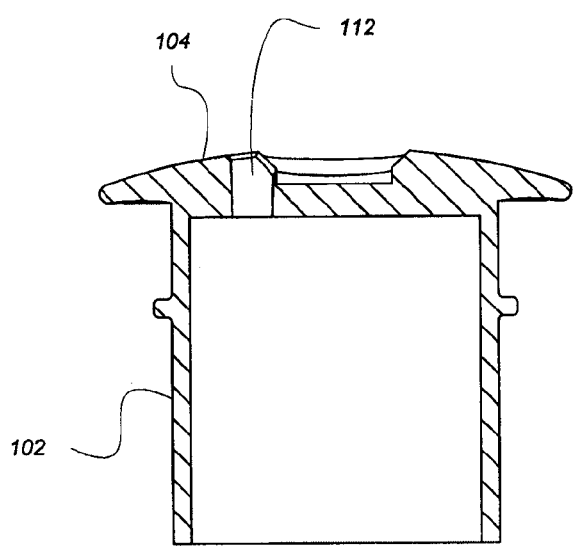
FIG. 10 shows a sectional view of the sealing device of FIG. 7.

According to embodiments, and as shown in FIGS. 4 and 10, guidewire channel 112 may extend through sealing device 100 and shaft 20 of intragastric device 10. Guidewire channel 112 may be configured to accommodate a guidewire for assisted delivery and management of intragastric device 10 during implant, explant, or maintenance thereof According to embodiments, sealing device 100 may be provided to selectably seal an end of intragastric device 10. As shown in FIGS. 5-6 and 9-10, sealing device 100 may include body 102 and head 104. Body 102 and head 104 may be fixably connected to each other. Body 102 may be selectably or fixedly attached to at least a portion of shaft 20 or intragastric device 10.

According to embodiments, and as shown in FIGS. 5-10, flange 106 may extend radially outward from portions of head 104 that do not otherwise exceed the circumferential limit of other components, such as body 102. Flange 106 may provide increased surface area and distribute forces applied at head 104 across a greater surface area. Flange 106 may be provided in a variety of geometries. For example, as shown in FIGS. 5-6 and 9-10, head 104 and flange 106 separately or together may form a substantially smooth, convex surface which may be viewed as an arc in cross-section. For example, the top surface of the head 104 may be configured in an arc such that imaginary extensions of such at least generally extend tangentially with the nearby surface of a balloon (as shown in FIGS. 3 and 4) so as to provide a smooth transition between the outer surfaces of head 104 and balloon 30*b*. Likewise, the plug 45 can have a flat surface (or a convex surface similar to the surface of the head 104 and flange 106) that substantially aligns with the nearby surface of a balloon so as to provide a smooth transition between the outermost surface of plug 45 and the balloon 30*a*. It is believed that geometries that form a step or a sizable gap between the surfaces of the head and balloon provide inflection points that result in trauma in a biological environment. As also shown in FIG. 4, the shape of walls of the balloons 30*a* and 30*b* may have a constant or near constant curvature as the surface of the balloon approaches the location of the sealing device 100 or plug 45. As shown in FIG. 4, the walls of the balloons 30*a* and 30*b* can be further curved proximate to the sealing device 100 or plug 45 so as to curve sharply towards the inside of the balloon to join to the shaft 20 at a position disposed about the body 102 of the sealing device or about the base of the plug.

The balloons may be formed to present a fully-deflated state and a fully-inflated state, or a series of partially-inflated or over-inflated states suitable for the use of the intragastric device. A fully deflated state disposes the balloon so that it is pressed against or disposed loosely about the surface of the shaft so as to present a low profile facilitating delivery. In a fully-inflated state, the balloon presents a profile in which the curvature of the surface of the balloon aligns with the curvature of the sealing device so as to minimize inflection points. In an over-inflated state, that balloon extends beyond the position observed with the fully-inflated state so as to present a balloon surface that curves inwardly towards an inwardly disposed sealing device. The balloon may also be formed of a material, or reinforced with a material, that limits the inflation of the balloon to a predetermined fully-inflated state, or that prevents further expansion of the balloon once the balloon achieves a fully-inflated state. The balloon may also be constructed of a flexible non-expandable material that is in a folded stated when deflated and in an fully unfolded state when fully inflated.

Figure 7:
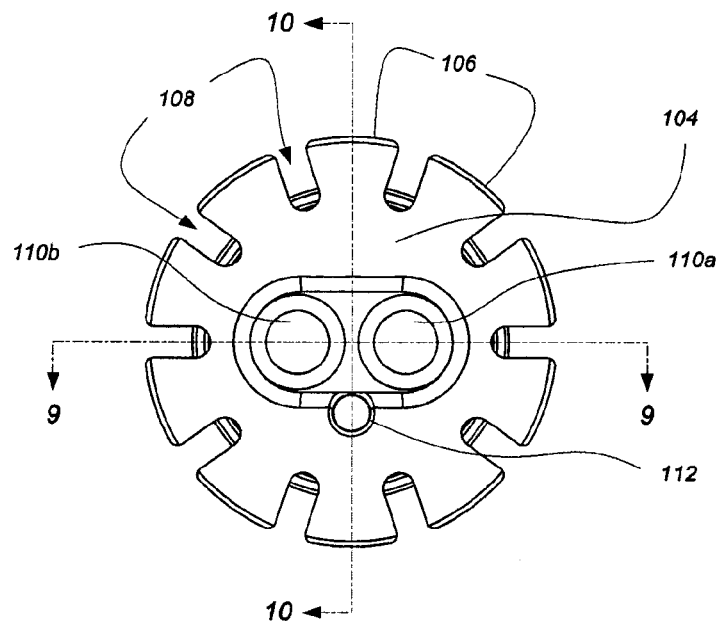
FIG. 7 shows a top view of a sealing device.
Figure 8:
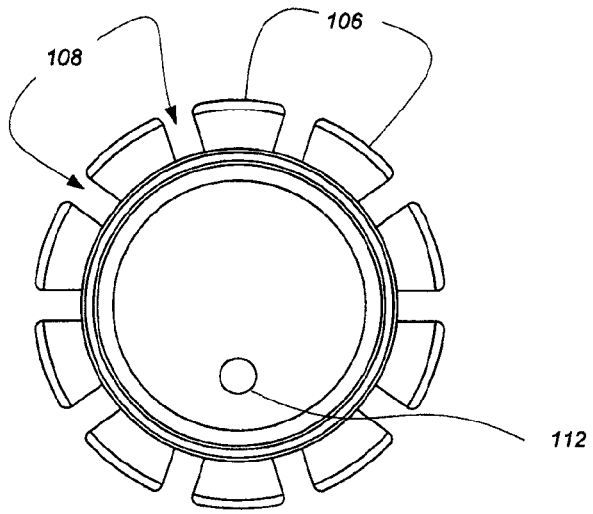
FIG. 8 shows a bottom view of a sealing device.

According to embodiments, and as shown in FIGS. 7 and 8, flange 106 may include interruptions 108, such as tabs, around at least a portion of a perimeter of head 104. Interruptions 108 may be configured to further distribute forces applied at head 104. Interruptions 108 may further be configured to facilitate securement and interfacing with a securement device such as a snare, such that a portion of the snare is disposed within an interruption. For example, a snare configured to secure by radial constriction may better secure to sealing device 100 by way of at least one of interruptions 108.

Figure 5:
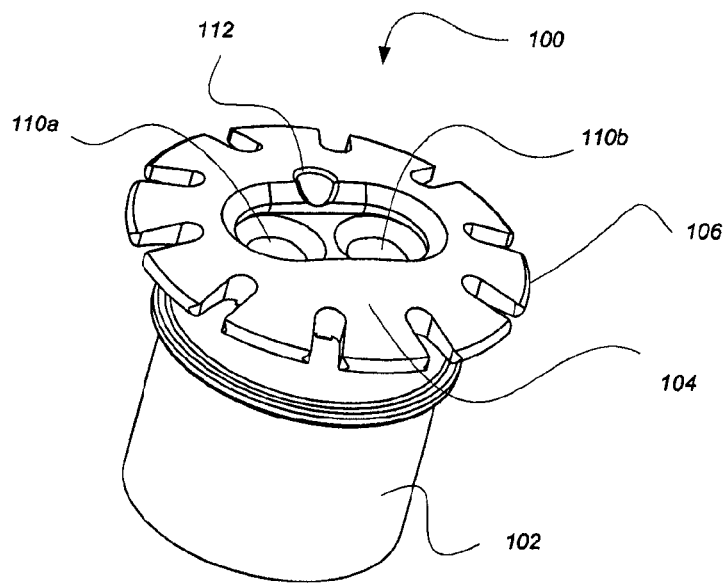
FIG. 5 shows a perspective view of a sealing device.
Figure 6:
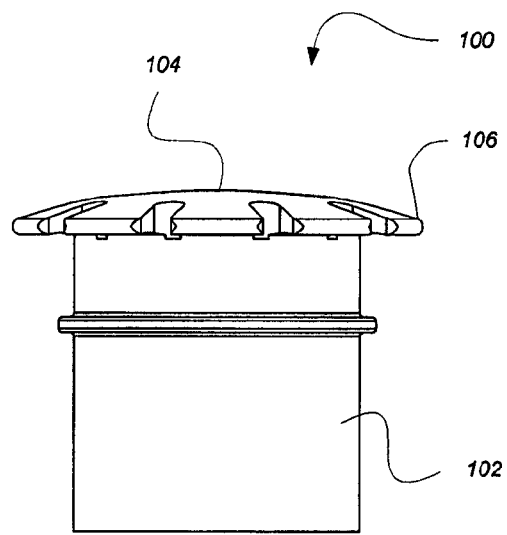
FIG. 6 shows a side view of a sealing device.

According to embodiments, and as shown in FIGS. 5, 7, and 9, at least one membrane may be provided to cover a corresponding lumen and provide controlled access by an aspiration device. For example, first membrane 110*a* may be configured to cover first lumen 40*a* at an end of the lumen (i.e., at first aspiration port 48*a*). Likewise, second membrane 110*b* may be configured to cover second lumen 40*b* at an end of the lumen (i.e., at second aspiration port 48*b*). Such a condition may define a "closed state" of the membrane. The membrane may be of thin walls to provide selective access to the corresponding lumen for aspiration of the lumen by controlled crossing, penetration, or breach of the membrane. Such a condition may define an "open state" of the membrane. The measure of thinness may be determined by the nature of materials used and known pressure conditions during inflation of intragastric device 10. Accordingly, membranes may be of a rigid, semi-rigid, or flexible material to facilitate aspiration procedures. According to embodiments, membranes and surrounding structure may facilitate controlled aspiration by providing a sufficiently thin or flexible membrane that permits crossing, penetration, or breach of the membrane by an aspiration device while resisting undesirable rupture of the membrane beyond the locality of the aspiration device under pressurized conditions.

Figure 9A:
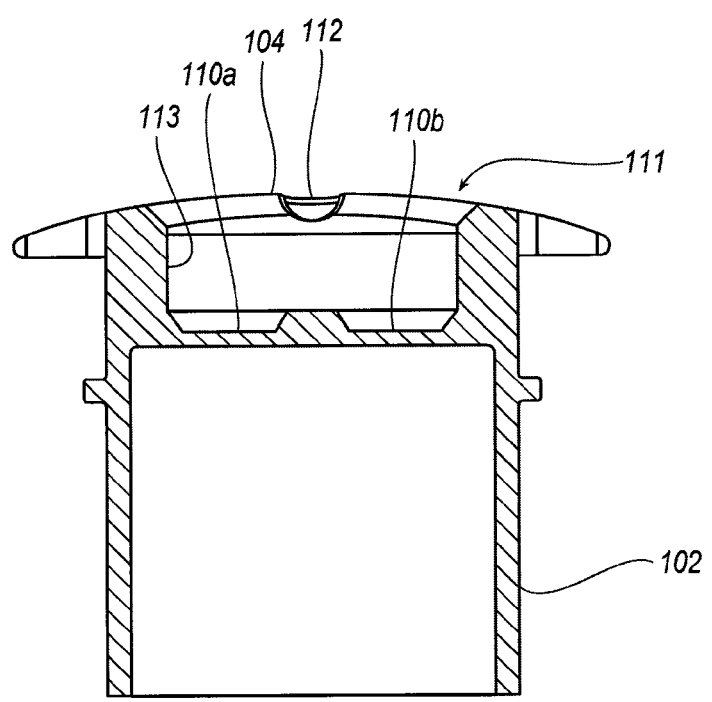
FIG. 9A shows an alternative sectional view of the sealing device of FIG. 7.

According to embodiments, membranes may be of a variety of geometries, including flat, as shown in FIG. 9, convex (not shown), or concave (not shown). For example, an inner surface may be configured to extend into a corresponding lumen. By further example, an outer surface may be shaped to naturally guide an aspiration device to a desired location for subsequent operations. As shown in FIG. 9A, the first membrane 110*a* and second membrane 110*b* may be disposed with in a recess 111 so that the walls 113 of the recess 111 guide an aspiration device into an engagement with the intragastric device before the membranes are engaged. According to embodiments, membranes may be configured to adequately seal each corresponding lumen to retain fluids therein and avoid inadvertent evacuation of fluids out of intragastric device 10 or into other lumens. According to embodiments, membranes may be self-sealing, such that a sufficiently small hole pierced therein may recover a sealed state when the piercing object is removed. Such self-sealing may be facilitated by the nature of at least a portion of the fluid present at the membrane.

According to embodiments, any number of membrane layers may be provided. Where a plurality of layers are present, each layer may have disparate characteristics, such as rigidity, flexibility, expansion, porosity, etc. For example, two or more layers may cover ends of an inner layer that may have enhanced self-sealing characteristics by expanding when exposed to fluids caused by breach of the surrounding layers.

According to embodiments, methods of inflating and aspirating balloon device 10 are disclosed. According to embodiments, intragastric device 10 may be provided with balloons (e.g., first balloon 30*a* and second balloon 30*b*) in a deflated state. Sealing device 100 may be provided installed onto intragastric device 10.

According to embodiments, intragastric device 10 may be provided to a gastric cavity of a patient and inflated. An insufflation fluid may be provided to balloons via inflation ports, lumens, and openings. Where sleeves (e.g., first sleeve 50*a* and second sleeve 50*b*) and barriers (e.g., first barrier 46*a* and second barrier 46*b*) are provided, fluid may travel from inflation chambers (e.g., first inflation chamber 42*a* and second inflation chamber 42*b*) through inflation openings (e.g., first inflation opening 32*a* and second inflation opening 32*b*) and past sleeves (e.g., first sleeve 50*a* and second sleeve 50*b*) to inflate balloons. Where aspiration openings (e.g., first aspiration opening 34*a* and second aspiration opening 34*b*) and aspiration chambers (e.g., first aspiration chamber 44*a* and second aspiration chamber 44*b*) are provided, fluid may flow there through during inflation or be restricted from the same until an aspiration process.

Figure 11:
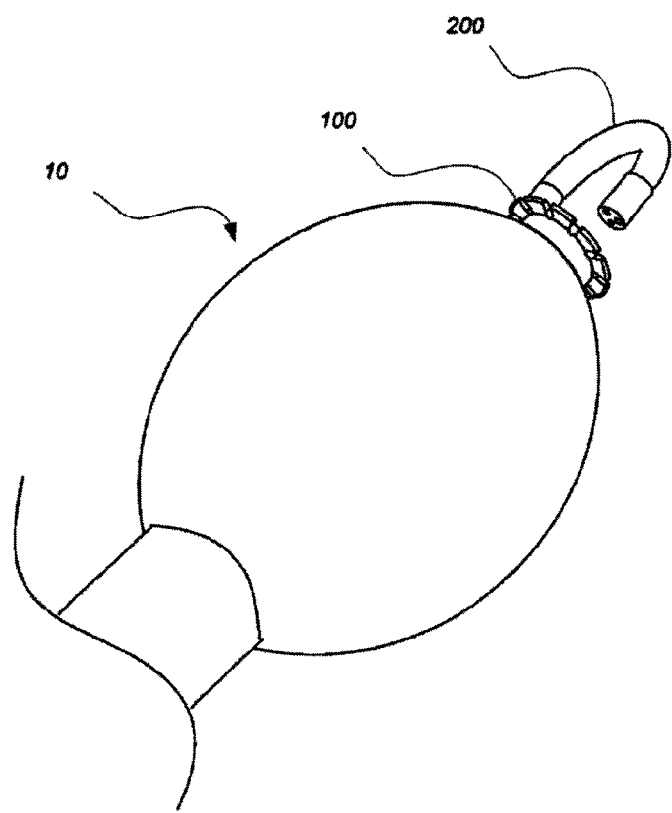
FIG. 11 shows a partial perspective view of an intragastric device.

According to embodiments, a method for aspirating and explanting intragastric device 10 after emplacement and inflation thereof is disclosed. According to embodiments, and as shown in FIG. 11, endoscope 200 may be provided to view and interact with sealing device 100 of intragastric device 10. Where sealing device 100 is at an end of intragastric device 10 that is distally located from an entrance point into the gastric cavity, a standard endoscope in a retroflexed position (e.g., a "U-turn" shaped endoscope) may be used, as shown in FIG. 11. Endoscope 200 may provide a variety of structures and functions, including visualization, working channels, and devices as disclosed further herein.

Figure 12:
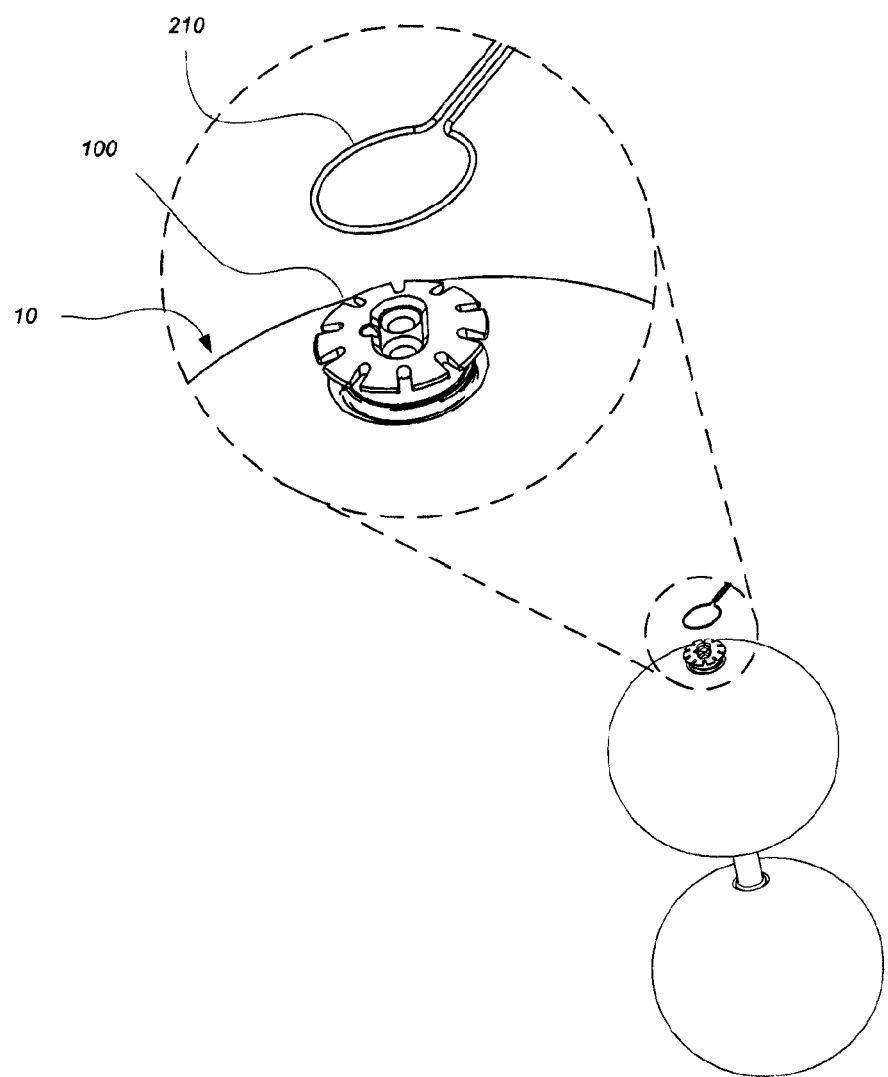
FIG. 12 shows a perspective view of an intragastric device with a magnified view of a sealing device and a snare device.

According to embodiments, and as shown in FIG. 12, a snare 210 may be deployed from endoscope 200 and secured to at least a portion of sealing device 100. For example, snare 210 may be secured onto at least one of head 104, at least one flange 106, and at least one interruption 108, including combinations thereof. Where initial securement is not satisfactory, partial securement may be used to reposition intragastric device 10 or sealing device 100 prior to re-securement. Those having skill in the art will recognize that a variety of devices, tools, and structures may be used to engage and operate on sealing device 100 from endoscope 200. For example, snare 210 may be any snare, grasper, forceps, needle, or other securing device for interfacing with at least a portion of sealing device 100.

Figure 13:
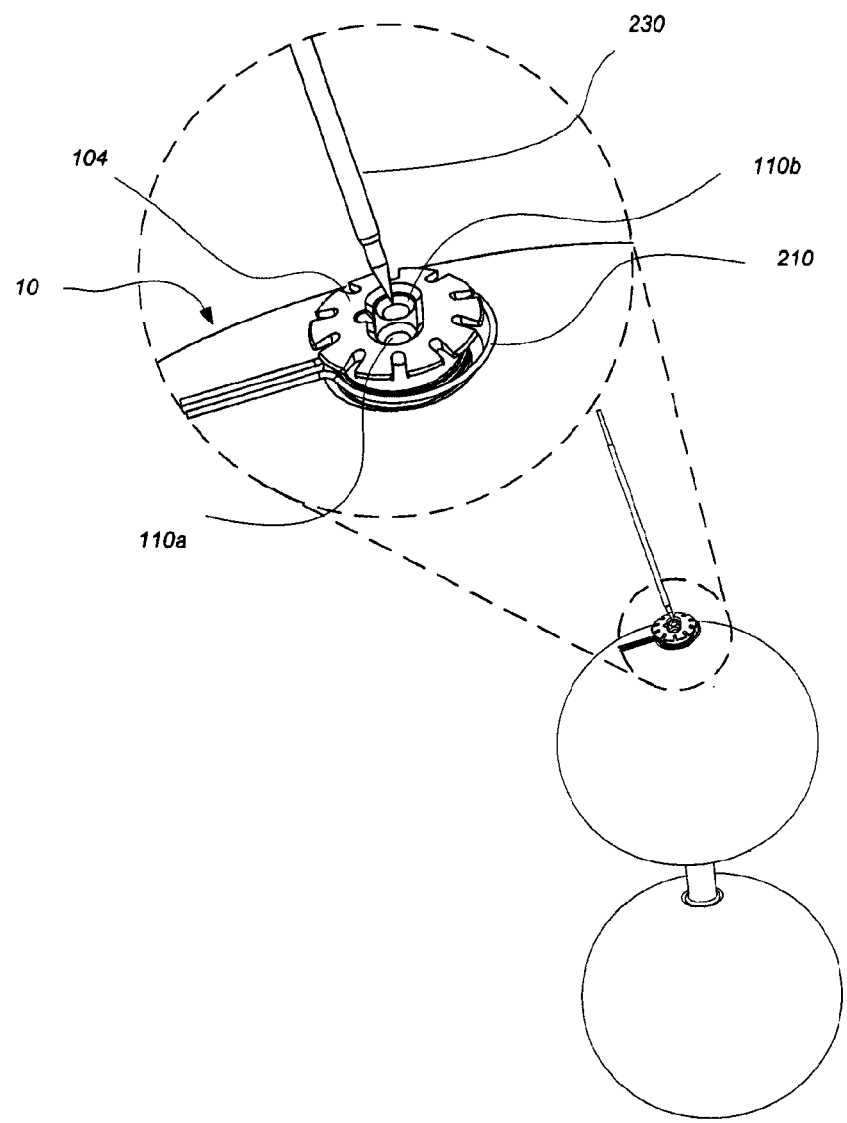
FIG. 13 shows a perspective view of an intragastric device with a magnified view of a sealing device and an aspiration device.
Figure 19:
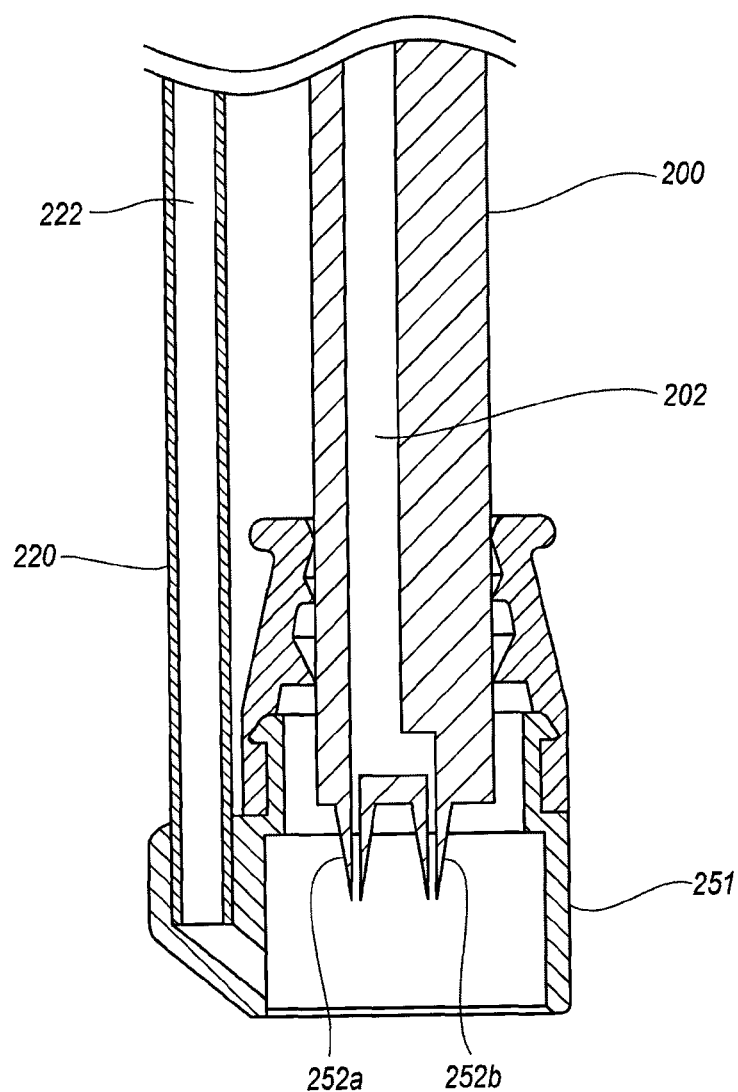
FIG. 19 shows a partial sectional view of an endoscope with an alternative configuration.

According to embodiments, and as shown in FIG. 13, aspiration device 230 may be provided to engage sealing device 100. Aspiration device 230 may perform controlled crossing, penetration, or breach of a membrane to access a corresponding lumen by aspiration device 230 or another device. Such action may facilitate localized evacuation of fluids, as opposed to uncontrolled rupture of the surface of an inflated balloon, where widespread rupture and uncontainable release of fluids is common due to the pressure conditions thereof. The aspiration device 230 may be directed into position to breach the membrane by guiding walls of a recess surrounding the membranes. The walls of the recess may guide the aspiration device 230 into alignment with the membranes before breaching the membranes.

According to embodiments, suction device 220 may be provided with endoscope 200 for operation on intragastric device 10, as shown in FIGS. 14-18. Suction device 220 may be compatible with, attachable to, a component of, or an integral part of endoscope 200. For example, suction device 220 and endoscope 200 may provide workspace 250 when brought to a portion of intragastric device 10, such as sealing device 100, before, during, or after opening at least one lumen of intragastric device 10. Suction device 220 may cause fluid released from intragastric device 10 to actively or passively be directed to a desired location (e.g., through endoscope vacuum channel 222 or working lumen 202 to a reservoir). Accordingly, pressure at a distal end of suction device 220 may be managed by any variety of devices, such as at a proximal end of suction device 220. Suction device 220 may cover all or part of the exposed portions of sealing device 100. Suction device 220 may mate onto or within at least one lumen to controllably aspirate fluid from intragastric device 10. In an alternative embodiment shown in FIG. 19, the workspace 251 may be configured to have an internal shape or internal diameter that corresponds to the outer shape or outer diameter of the body 102, so as to facilitate the insertion of a portion of the sealing device 100 (such as the sealing device shown in FIG. 9) into the workspace 251 and to align the first membrane 110*a* with first aspiration interface 252*a* and align the second membrane 110*b* with second aspiration interface 252*b*.

According to embodiments, accessing at least one lumen of intragastric device 10 may cause fluid from within a corresponding balloon thereof to be capable of deflation. For example, a lumen that has been accessed may be in fluid communication with an interior portion of a balloon via an opening. According to embodiments, accessing at least one lumen of intragastric device 10 may cause automatic deflation of a balloon based on a tendency of the balloon to contract or constrict or based on a pressure differential between the interior and exterior of the balloon. According to embodiments, a suction device 220 may be provided over sealing device 100 before, during, or after accessing at least one lumen. The suction device may cause fluid released to actively or passively be directed to a desired location (e.g., through endoscope 200 to a reservoir). Accordingly, pressure at a distal end of the suction device may be managed by any variety of devices, such as at a proximal end thereof. The suction device may cover all or part of the exposed portions of sealing device 100. The suction device may mate onto or within at least one lumen or membrane to controllably aspirate fluid from intragastric device 10. For example, a lumen may be provided within aspiration device 230 as a conduit for fluid.

According to embodiments, where membranes are of a self-sealing configuration, retraction of aspiration device 230 may result in at least substantial recovery of a seal over a corresponding lumen.

According to embodiments, partial or full deflation of intragastric device 10 may facilitate subsequent explant, removal, or adjustment thereof. According to embodiments, intragastric device 10 may be removed along with endoscope 200 after deflation.

According to embodiments, a kit of parts is disclosed, including components disclosed herein, for use by a user. Included in the kit may be instructions for use.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

We claim:

1. An intragastric balloon device, comprising:
   a shaft having a plurality of lumens including at least a first lumen and a second lumen;
   a plurality of balloons including at least a first balloon at one end of the shaft and a second balloon at another end of the shaft, wherein an interior portion of the first balloon is in fluid communication with the first lumen and an interior portion of the second balloon is in fluid communication with the second lumen; and
   a sealing device comprising a body engaging at least one of the shaft, the first balloon, and the second balloon, a head extending from the body and supporting at least one membrane configured to seal an aspiration port of one of the first or second lumens when the at least one membrane is in a first state and further configured to provide fluidic access to at least one of the first and second lumens when the at least one membrane is in a second state.

2. The intragastric balloon device of claim 1, wherein the first lumen communicates with a first inflation port and the second lumen communicates with a second inflation port.

3. The intragastric balloon device of claim 1, wherein the first balloon is in fluid communication with the first lumen via a first inflation opening, and the second balloon is in fluid communication with the second lumen via a second inflation opening.

4. The intragastric balloon device of claim 1, wherein the first lumen is divided into a first inflation chamber and a first aspiration chamber by a barrier disposed in the first lumen, and the second lumen is divided into a second inflation chamber and a second aspiration chamber by a barrier disposed in the second lumen.

5. The intragastric balloon device of claim 4, wherein the first balloon is in fluid communication with the first inflation chamber via a first inflation opening, and the second balloon is in fluid communication with the second inflation chamber via a second inflation opening.

6. The intragastric balloon device of claim 4, wherein the first balloon is in fluid communication with the first aspiration chamber via a first aspiration opening, and the second balloon is in fluid communication with the second aspiration chamber via a second aspiration opening.

7. The intragastric balloon device of claim 1, further comprising a first sleeve disposed within the first balloon to cover at least a portion of the first aspiration opening.

8. The intragastric balloon device of claim 1, further comprising a guidewire channel extending through the shaft and the sealing device.

9. The intragastric balloon device of claim 1, further comprising:
   a plug engaging at least one of the shaft, the first balloon, and the second balloon, the plug being opposite the sealing device; and
   a guidewire channel extending through the plug and the sealing device.

10. The intragastric balloon device of claim 1 wherein the sealing device is attached to a proximal end of the shaft.

11. The intragastric balloon device of claim 1 wherein the sealing device is attached to a distal end of the shaft.

* * * * *